United States Patent
Zhang et al.

(10) Patent No.: US 12,049,978 B2
(45) Date of Patent: Jul. 30, 2024

(54) PROFILE DISCONNECTION

(71) Applicant: SAINT-GOBAIN PERFORMANCE PLASTICS CORPORATION, Solon, OH (US)

(72) Inventors: Jianfeng Zhang, Shrewsbury, MA (US); Rachel Z. Pytel, Newton, MA (US); Jian L. Ding, Stow, MA (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 521 days.

(21) Appl. No.: 17/130,167

(22) Filed: Dec. 22, 2020

(65) Prior Publication Data

US 2021/0207754 A1 Jul. 8, 2021

Related U.S. Application Data

(60) Provisional application No. 62/954,167, filed on Dec. 27, 2019.

(51) Int. Cl.
*F16L 55/10* (2006.01)
*F16L 11/12* (2006.01)

(52) U.S. Cl.
CPC .......... *F16L 55/1003* (2013.01); *F16L 11/12* (2013.01)

(58) Field of Classification Search
CPC ............... F16L 55/1003; F16L 11/12
See application file for complete search history.

(56) References Cited

U.S. PATENT DOCUMENTS

| | | | |
|---|---|---|---|
| 4,325,417 A | 4/1982 | Boggs et al. | |
| 4,384,186 A | 5/1983 | Burt | |
| 5,741,458 A * | 4/1998 | Rowley | F24D 3/146 |
| | | | 264/296 |
| 5,993,593 A | 11/1999 | Swartz et al. | |
| 6,113,782 A | 9/2000 | Leonard | |
| 7,226,649 B2 | 6/2007 | Shang et al. | |
| 7,442,271 B2 | 10/2008 | Asmussen et al. | |
| 10,195,416 B2 | 2/2019 | Gebauer et al. | |
| 2005/0017505 A1 | 1/2005 | Thilly | |
| 2007/0233041 A1 | 10/2007 | Gellman | |
| 2007/0233172 A1 | 10/2007 | Gellman | |

(Continued)

FOREIGN PATENT DOCUMENTS

| | | |
|---|---|---|
| CN | 103492021 A | 1/2014 |
| CN | 106029128 A | 10/2016 |

(Continued)

OTHER PUBLICATIONS

English machine translation for CN107325442A. (Year: 2017).*

(Continued)

*Primary Examiner* — Michael C Miggins
(74) *Attorney, Agent, or Firm* — Abel Schillinger, LLP; Chi Suk Kim

(57) ABSTRACT

A profile includes: a sidewall, a lumen for a fluid path, and an end, the profile including a thermoset material, wherein the profile includes a sealed end without an external bonding material, wherein the sealed end withstands a seal integrity pressure test of at least 1 psi, such as at least 5 psi, such as at least 10 psi, such as at least 15 psi, or even at least 20 psi air pressure for about 30 minutes under dry and wet conditions.

12 Claims, 2 Drawing Sheets

(56) References Cited

U.S. PATENT DOCUMENTS

| | | | |
|---|---|---|---|
| 2009/0131854 A1 | 5/2009 | DiCarlo et al. | |
| 2013/0019864 A1 | 1/2013 | Wondka | |
| 2014/0077488 A1 | 3/2014 | Wegener et al. | |
| 2016/0030728 A1 | 2/2016 | Bourgeois et al. | |
| 2016/0167289 A1 | 6/2016 | Cassiday et al. | |
| 2016/0199568 A1 | 7/2016 | McNall, III et al. | |
| 2016/0271312 A1 | 9/2016 | Lance et al. | |
| 2018/0161554 A1 | 6/2018 | Takemoto et al. | |
| 2018/0361054 A1 | 12/2018 | Roxas | |
| 2019/0105148 A1 | 4/2019 | Lu et al. | |
| 2021/0207754 A1* | 7/2021 | Zhang | F16L 55/1003 |

FOREIGN PATENT DOCUMENTS

| | | | |
|---|---|---|---|
| CN | 106795343 A | 5/2017 | |
| EP | 3446861 A1 | 2/2019 | |
| WO | 2015075040 A1 | 5/2015 | |

OTHER PUBLICATIONS

International Search Report and Written Opinion for PCT Application No. PCT/US2020/066532, mailed Apr. 16, 2021, 9 pages.

Archer, G., "Blood Transfusion Guide", Tianjin Science and Technology Translation and Publishing Company, Apr. 30, 1998, 3 pages.

\* cited by examiner

PROFILE DISCONNECTION

CROSS-REFERENCE TO RELATED APPLICATION(S)

This application claims priority under 35 U.S.C. § 119(e) to U.S. Provisional Patent Application No. 62/954,167, entitled "PROFILE DISCONNECTION", by Jianfeng ZHANG et al., filed Dec. 27, 2019, which is assigned to the current assignee hereof and incorporated herein by reference in its entirety.

FIELD OF THE DISCLOSURE

The disclosure, generally, is related to a profile and a method providing a sterile terminus of a profile.

BACKGROUND

Many industries utilize sterile connections for the delivery and removal of fluids. Since sterile connections may be used in a variety of industries, such as the medical industry and pharmaceutical industry, thermoplastic and thermoset elastomers are typically used that are non-toxic, flexible, thermally stable, have low chemical reactivity, and can be produced in a variety of sizes. In many instances, it is desirable to disconnect a profile to create a sterile seal. Unfortunately, it is difficult to effectively provide a seal with a thermoset elastomeric material. In particular, a silicone elastomer is a thermoset material that cannot be melted and thus, cannot be sealed with conventional high temperature methods and in many cases, an external bonding material such as an adhesive or a mechanical clamp is used. As such, it is a challenge to maintain any sterility and an effective seal, especially when sealing with an adhesive and/or a mechanical clamp.

Accordingly, an improved sterile seal and method of providing a seal for a thermoset material is desired.

SUMMARY

In an embodiment, a profile includes: a sidewall, a lumen for a fluid path, and an end, the profile including a thermoset material, wherein the profile includes a sealed end without an external bonding material, wherein the sealed end withstands a seal integrity pressure test of at least 1 psi, such as at least 5 psi, such as at least 10 psi, such as at least 15 psi, or even at least 20 psi air pressure for about 30 minutes under dry and wet conditions.

In an embodiment, a profile includes a sidewall, a lumen for a fluid path, and an end, the profile including a thermoset material, wherein the profile includes a sealed end without an external bonding material, wherein the sealed end has a mechanical strength greater than or equal to a mechanical strength of the sidewall.

In another embodiment, a method of a providing a sterile terminus of a profile includes: providing the profile having a sidewall, a lumen for a fluid path, and an end, the profile including a thermoset material; providing a surface activation treatment to a surface adjacent to the end of the profile; and sealing the end to provide the terminus of the lumen, wherein the sealed end has a mechanical strength greater than or equal to a mechanical strength of the sidewall.

In yet another embodiment, a method of a providing a sterile disconnection of a profile includes: providing the profile having a sidewall and a lumen for a fluid path, the profile including a thermoset material; cutting the profile to create an end; providing a surface activation treatment to a surface adjacent to the end of the profile; and sealing the end to provide a terminus of the lumen, wherein the sealed end has a mechanical strength greater than or equal to a mechanical strength of the sidewall.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1A:
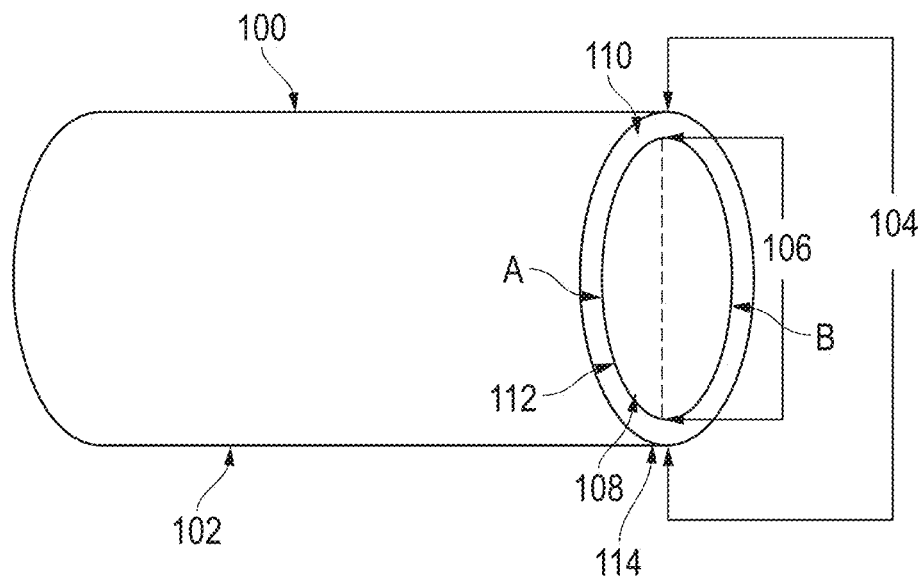
FIGS. 1A and 1B include illustrations of an exemplary profile.

The following description in combination with the figures is provided to assist in understanding the teachings disclosed herein. The following discussion focuses on specific implementations and embodiments of the teachings. This focus is provided to assist in describing the teachings and should not be interpreted as a limitation on the scope or applicability of the teachings.

As used herein, the terms "comprises", "comprising", "includes", "including", "has", "having", or any other variation thereof, are open-ended terms and should be interpreted to mean "including, but not limited to . . . ." These terms encompass the more restrictive terms "consisting essentially of" and "consisting of." In an embodiment, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in reference books and other sources within the structural arts and corresponding manufacturing arts. Unless indicated otherwise, all measurements are at about 25° C. For instance, values for viscosity are at 25° C., unless indicated otherwise.

The disclosure generally relates to a profile. The profile includes a sidewall, a lumen for a fluid path, and an end. The profile includes a polymeric material. In a particular embodiment, the polymeric material includes a thermoset material. The profile includes a sealed end without an external bonding material. In an embodiment, the sealed end has a mechanical strength greater than or equal to a mechanical strength of the sidewall. For instance, the strength as a physical barrier of the sealed end is greater than or equal to the strength of a physical barrier of the sidewall. The sealed end is provided via a surface activation treatment. The "sealed end" is a point of the profile where fluid cannot flow through. "Fluid" as used herein refers to any flowable material and includes, but is not limited to, liquid, gas, powder, solid, or combination thereof.

In an embodiment, the surface activation treatment provides the sealed end of the profile. Any surface activation treatment is envisioned and includes any processing input energy to a surface of the profile. In an embodiment, the processing input energy is with wave irradiation, particle irradiation, or combination thereof. In an embodiment, the wave irradiation includes any wave irradiation envisioned such as radio waves, microwaves, infrared, visible light, ultraviolet, x-rays, gamma radiation, or combination thereof. In a particular embodiment, the wave irradiation includes microwaves, ultraviolet, x-rays, gamma radiation, or combination thereof. In an embodiment, the particle irradiation includes alpha radiation, beta radiation, charged ions, neutron radiation, or combination thereof. In another embodiment, the particle irradiation includes corona treatment, ion treatment, plasma treatment, or combination thereof.

The surface activation treatment provides an effective seal at the point of surface treatment and compression point of the treated surface. In a particular embodiment, an inner surface of the end of the profile is surface treated and the end of the profile is compressed to provide the seal. The compressed end that has been surface treated adheres together and provides a flat seal. The efficacy of the seal provides advantageous mechanical and physical properties at the end of profile. For instance, the sealed end withstands a seal integrity pressure test of at least 1 psi, such as at least 5 psi, such as at least 10 psi, such as at least 15 psi, or even at least 20 psi air pressure for about 30 minutes under dry and wet conditions, as described further in the Examples. In an embodiment, the sealed end maintains a burst of at least about 10%, such as at least about 15%, such as at least about 25%, or even at least about 50%, compared to a burst of the sidewall. In a particular embodiment, the sidewall bursts before burst at the seal. In yet another embodiment, the sealed end has an adhesion force of at least about 5 ppi (pounds per inch), such as at least about 10 ppi, such as at least about 15 ppi, at least about 50 ppi, or even at least 300 ppi as described via peel test conditions in the Examples.

In an embodiment, the surface treatment provides sterility to the surface it treats, i.e. sterilizes the treated surface. A "treated surface" as used herein refers to any surface that is exposed to surface activation treatment. In an embodiment, "providing sterility" includes maintaining sterility for a pre-sterilized profile. In a particular embodiment, the surface activation treatment provides a sterile disconnection of the profile.

In an embodiment, any profile is envisioned. In an embodiment, at least one profile has at least one lumen for fluid flow through. For instance, the profile is any connector, a tube, a port, a hose, a catheter, and the like. In an embodiment, the profile is a tube. In an example, the profile may be a single homogenous polymeric material. In an embodiment, the profile may be a multi-layered composite material, for example, including more than one distinct polymeric layer.

In an embodiment, the profile includes a polymeric material. Any polymeric material is envisioned. In an embodiment, the polymeric material includes a thermoplastic elastomer, a thermoset elastomer, or combination thereof. In an embodiment, the polymeric material is a thermoset elastomer. Any thermoset elastomer is envisioned. In a particular embodiment, the thermoset elastomer includes a silicone elastomer, a dine elastomer, a butyl rubber, a natural rubber, a polyurethane rubber, an ethylene propylene diene monomer rubber, an isoprene rubber, a nitrile rubber, a styrene butadiene rubber, a halogenated rubber, a blend, or combination thereof. Any rubber for medical/pharmaceutical applications is envisioned. In a particular embodiment, the polymeric material includes a silicone elastomer.

A typical silicone elastomer includes a silicone matrix component. An exemplary silicone matrix component includes a polyorganosiloxane. An exemplary polyorganosiloxane includes a polyalkylsiloxane, a polyarylsiloxane, or combination thereof. Any reasonable polyalkylsiloxane is envisioned. Polyalkylsiloxanes include, for example, silicone polymers formed of a precursor, such as dimethylsiloxane, diethylsiloxane, dipropylsiloxane, methylethylsiloxane, methylpropylsiloxane, or combinations thereof. In a particular embodiment, the polyalkylsiloxane includes a polydialkylsiloxane, such as polydimethylsiloxane (PDMS). In a particular embodiment, the polyalkylsiloxane is a silicone hydride-containing polyalkylsiloxane, such as a silicone hydride-containing polydimethylsiloxane. In a further embodiment, the polyalkylsiloxane is a vinyl-containing polyalkylsiloxane, such as a vinyl-containing polydimethylsiloxane. The vinyl group may be an endblock of the polyalkylsiloxane, on chain of the polyalkylsiloxane, or any combination thereof. In yet another embodiment, the silicone matrix component is a combination of a hydride-containing polyalkylsiloxane and a vinyl-containing polyalkylsiloxane.

In an embodiment, the polymeric material is a thermoset elastomer and more particularly, a diene elastomer. The diene elastomer may be a copolymer formed from at least one diene monomer. For example, the diene elastomer may be a copolymer of ethylene, propylene and diene monomer (EPDM), a thermoplastic EPDM composite, or combination thereof. An exemplary diene monomer may include a conjugated diene, such as butadiene, isoprene, chloroprene, or the like; a non-conjugated diene including from 5 to about 25 carbon atoms, such as 1,4-pentadiene, 1,4-hexadiene, 1,5-hexadiene, 2,5-dimethyl-1,5-hexadiene, 1,4-octadiene, or the like; a cyclic diene, such as cyclopentadiene, cyclohexadiene, cyclooctadiene, dicyclopentadiene, or the like; a vinyl cyclic ene, such as 1-vinyl-1-cyclopentene, 1-vinyl-1-cyclohexene, or the like; an alkylbicyclononadiene, such as 3-methylbicyclo-(4,2,1)-nona-3,7-diene, or the like; an indene, such as methyl tetrahydroindene, or the like; an alkenyl norbornene, such as 5-ethylidene-2-norbornene, 5-butylidene-2-norbornene, 2-methallyl-5-norbornene, 2-isopropenyl-5-norbornene, 5-(1,5-hexadienyl)-2-norbornene, 5-(3,7-octadienyl)-2-norbornene, or the like; a tricyclodiene, such as 3-methyltricyclo $(5,2,1,0^2,6)$-deca-3,8-diene or the like; or any combination thereof.

In a particular embodiment, the polymeric material is a thermoplastic elastomer and includes a polystyrene, a polyester, a silicone copolymer, silicone thermoplastic vulcanizate, a copolyester, a polyamide, a fluoropolymer, a polyolefin, a polyether-ester copolymer, a thermoplastic urethane, a polyether amide block (PEBA) copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or combination thereof. In an embodiment, the polymeric material includes a styrene block copolymer blended with a polyolefin, such as a polypropylene.

In an embodiment, the polymeric material is a fluoropolymer. An exemplary fluoropolymer includes a copolymer of a poly vinylidene fluoride (PVDF) and a hexafluoropropylene (HFP), a polytetrafluoroethylene (PTFE), a fluorinated ethylene propylene copolymer (FEP), a copolymer of tetrafluoroethylene and perfluoropropyl vinyl ether (PFA), a copolymer of tetrafluoroethylene and perfluoromethyl vinyl ether (MFA), a copolymer of ethylene and tetrafluoroethylene (ETFE), a copolymer of ethylene and chlorotrifluoroethylene (ECTFE), a polychlorotrifluoroethylene (PCTFE), a poly vinylidene fluoride (PVDF), a terpolymer including a tetrafluoroethylene, a hexafluoropropylene, and a vinylidenefluoride (THV), a polyvinyl fluoride (PVF, e.g., Tedlar™), a terpolymer of tetrafluoroethylene, hexafluoropropylene, and ethylene, any blend, any alloy, or combination thereof.

In a particular embodiment, the polymeric material includes a polyolefin. A typical polyolefin may include a homopolymer, a copolymer, a terpolymer, an alloy, or any combination thereof formed from a monomer, such as ethylene, propylene, butene, pentene, methyl pentene, octene, or any combination thereof. An exemplary polyolefin includes a polyethylene, high density polyethylene (HDPE), medium density polyethylene (MDPE), low density polyethylene (LDPE), ultra or very low density polyethylene (VLDPE), ethylene propylene copolymer, ethylene butene copolymer, polypropylene (PP), polybutene, polybutylene, polypentene, polymethylpentene, polystyrene, ethylene propylene rubber (EPR), ethylene octene copolymer, blend thereof, mixture thereof, and the like. The polyolefin further includes olefin-based random copolymers, olefin-based impact copolymers, olefin-based block copolymers, olefin-based specialty elastomers, olefin-based specialty plastomers, blends thereof, mixture thereof, and the like. In an example, the polyolefin includes polyethylene. In an example, the polyolefin includes polypropylene. In a particular example, the polyolefin is a random propylene copolymer. In an embodiment, the polyolefin is a gamma stabilized polypropylene.

In an additional example, the polymeric material may include a styrene block copolymer that includes, for example, a multiblock copolymer such as a diblock, triblock, polyblock, or any combination thereof. In a particular embodiment, the styrene block copolymer is a block copolymer having AB units. Typically, the A units are alkenyl arenes such as a styrene, an alpha-methylstyrene, para-methylstyrene, para-butyl styrene, or combination thereof. In a particular embodiment, the A units are styrene. In an embodiment, the B units include alkenes such as butadiene, isoprene, ethylene, butylene, propylene, or combination thereof. In a particular embodiment, the B units are ethylene, isoprene, or combinations thereof. Exemplary styrene block copolymers include triblock styrenic block copolymers (SBC) such as styrene-butadiene-styrene (SBS), styrene-isoprene-styrene (SIS), styrene-ethylene butylene-styrene (SEBS), styrene-ethylene propylene-styrene (SEPS), styrene-ethylene-ethylene-butadiene-styrene (SEEBS), styrene-ethylene-ethylene-propylene-styrene (SEEPS), styrene-isoprene-butadiene-styrene (SIBS), or combination thereof. In an embodiment, the styrene block copolymer is saturated, i.e. does not contain any free olefinic double bonds. In an embodiment, the styrene block copolymer contains at least one free olefinic double bond, i.e. an unsaturated double bond. In a particular embodiment, the styrene block copolymer is a styrene-ethylene based copolymer, a styrene isoprene based copolymer, a blend, or combination thereof.

Depending on the composition of the polymeric material, the polymeric material may be formed with any reasonable component such as any precursor with the addition of any reasonable additive. An additional additive includes, but is not limited to, a catalyst, a filler, a plasticizer, a lubricant, an antioxidant, a colorant, an optically transparent conductive additive, an adhesion promoter, heat stabilizer, acid scavenger, UV stabilizer, processing aid, or combination thereof. In a particular embodiment, the precursor, the additional additive such as the catalyst, the filler, plasticizer, lubricant, antioxidant, colorant, an optically transparent conductive additive, an adhesion promoter, heat stabilizer, acid scavenger, UV stabilizer, processing aid, or combination thereof are dependent upon the first polymeric material chosen and final properties desired for the profile.

Any reasonable catalyst that can initiate crosslinking of the polymeric material is envisioned. Exemplary catalysts include a catalyst that may be heat cured, IR radiation cured, e-beam cured, or combination thereof. The catalyst is dependent upon the polymeric material chosen. The catalyst may or may not be used in combination with a crosslinker promoter, such as triallyl cyanurate (TAC), triallyl isocyanurate (TAIC), or combination thereof. In an embodiment, the additive includes any reasonable adhesion promoter. Any reasonable adhesion promoter that promotes adhesion of adjacent surfaces is envisioned and is dependent upon the material chosen for the profile. Exemplary lubricants include silicone oil, waxes, slip aids, antiblock agents, the like, or any combination thereof. Exemplary lubricants further include silicone grafted polyolefin, polyethylene or polypropylene waxes, Oleic acid amide, erucamide, stearate, fatty acid esters, the like, or any combination thereof. Exemplary antioxidants include phenolic, hindered amine antioxidants. Exemplary fillers include calcium carbonate, talc, radio-opaque fillers such as barium sulfate, bismuth oxychloride, any combinations thereof, and the like. In an embodiment, the filler includes a functionalized filler. Exemplary functionalized fillers include, for example, a base filler that has a functional moiety that forms a chemical bond with the polymeric material. Any reasonable base filler is envisioned such as a silica filler, fumed silica filler, quartz, glass filler, aluminum (AlO(OH)), alumino-silicate, inorganic oxides, resinous filler, carbon black, graphite, graphene, carbon nanotube (CNT), fullerene or combination thereof. In a particular embodiment, the functionalized filler includes a silica filler. Any functional moiety is envisioned that has an adhesive affinity to the polymeric material. The functionalized moiety is, for example, a silane attached to the base filler, wherein the silane includes an acryl functional group, an epoxy functional group, a chloro functional group, or combination thereof. In an embodiment, any reasonable silane is envisioned and includes, for example, an alkoxysilane such as a trimethoxysilane, a triethoxysilane, or combination thereof. In an embodiment, the functionalized filler is a silicone-hydride attached to the base filler. In a particular embodiment, the silicone-hydride is trimethylsiloxy-terminated. When present as the functional moiety, any reasonable amount of functionalized filler is envisioned to provide an increased adhesive bond at the sealed end. In an embodiment, the functionalized filler forms a cohesive bond at the sealed end, i.e. cohesive failure occurs wherein the structural integrity of the sidewall of the profile fails before the sealed end fails. In an exemplary embodiment, the functionalized filler is mixed with the polymeric material to form a homogenous mixture of the functionalized filler contained with a matrix of the polymeric material. In an embodiment, the functionalized filler may or may not form a reactive and covalent bond with the polymeric material. In a more particular embodiment, the functionalized filler does not form a reactive and covalent bond with the polymeric material. Exemplary plasticizers include any known plasticizers such as a citrate, a phthalate, a trimellitate, 1,2-cyclohexane dicarboxylic acid diisonoyl ester (DINCH), an adipate, a polymeric plasticizer, a castor oil, a caster oil derivative, mineral oils, soybean oil, such as epoxidized soybean oil, the like, or any combination thereof.

Typically, the additional additive may be present at an amount of not greater than about 70% by weight of the total weight of the polymeric material, such as not greater than about 60% by weight of the total weight of the polymeric material, such as not greater than about 50% by weight of the total weight of the polymeric material, such as not greater than about 40% by weight of the total weight of the polymeric material, or even not greater than about 30% by weight of the total weight of the polymeric material. In an alternative embodiment, the polymeric material may be substantially free of an additional additive such as a catalyst, lubricant, a filler, a plasticizer, an antioxidant, a colorant, an adhesion promoter, heat stabilizer, acid scavenger, UV stabilizer, processing aid, or combination thereof. "Substantially free" as used herein refers to less than about 1.0% by weight, or even less than about 0.1% by weight of the total weight of the polymeric material.

FIG. 1A is a view of a profile 100 according to an embodiment. Typically, the profile 100 is any commercially available profile. In a particular embodiment, the profile 100 is in the form of a tube including a body 102 having an outside diameter 104 and an inner diameter 106. The inner diameter 106 can form a hollow bore 108 of the body 102. The hollow bore 108 defines a central lumen of the tube for fluid flowthrough. In addition, the body 102 is illustrated as a single layer, the single layer including the polymeric material. The body 102 can include a side wall 110 having a wall thickness that is measured by the difference between the outside diameter 104 and the inner diameter 106.

In a particular embodiment, the outside diameter 104 of the body 102 is about 0.025 inches to about 5.0 inches, such as about 0.15 inches to about 2.0 inches. It will be appreciated that the outside diameter 104 can be within a range between any of the minimum and maximum values noted above. In an embodiment, the inner diameter 106 of the body 102 is about 0.005 inches to about 4.0 inches, such as about 0.06 inches to about 1.0 inches. It will be appreciated that the inner diameter 106 can be within a range between any of the minimum and maximum values noted above. The wall thickness of the sidewall 110 is about 0.02 inches to about 4.0 inches, such as about 0.05 inches to about 1.0 inch, or even about 0.1 inches to about 0.5 inches. It will be appreciated that the wall thickness of the sidewall 110 can be within a range between any of the minimum and maximum values noted above.

Although the cross-section of the inner bore 108 perpendicular to an axial direction of the body 102 in the illustrative embodiment shown in FIG. 1A has a circular shape, the cross-section of the inner bore 108 perpendicular to the axial direction of the body 102 can have any cross-section shape envisioned. In an embodiment, the inner bore 108 can include an inner surface 112 of the profile 100.

Although illustrated as a single layer tube for the profile 100, any number of layers is envisioned. For instance, the profile includes one layer, two layers, three layers, or even a greater number of layers. Irrespective of the number of layers present, the outside diameter and inner diameter of the profile 100 can have any values as defined for the single layer tube 100 defined in FIG. 1A. The number of layers is dependent upon the final properties desired for the sterile terminus. Further, although illustrated as a single lumen, i.e. hollow bore 108 for the profile 100, any number of lumen is envisioned. For instance, the profile includes a plurality of lumen.

In an embodiment, the profile 100 may further include other layers. Other layers include, for example, a polymeric layer, a reinforcing layer, an adhesive layer, a barrier layer, a chemically resistant layer, a metal layer, any combination thereof, and the like. Any additional layer is envisioned and is dependent upon the material chosen. In an embodiment, any number of polymeric layers is envisioned.

In an embodiment, a method of providing a sterile terminus is provided. A method of providing a sterile disconnection is also provided. The method includes providing the profile 100 having the sidewall 110, a lumen for a fluid path through central bore 108, and an end 114. In a particular embodiment, a surface activation treatment is provided. For instance, the surface activation treatment is provided on the inner surface 112 of the profile 100. In a particular embodiment, the inner surface 112 of the end 114 is surface treated. In a more particular embodiment, an entire circumference of the inner surface 112 of the end 114 is surface treated. With the entire circumference of the inner surface 112 of the end 114 being treated, when the treated surface is compressed and comes into contact with another portion of the treated surface, an effective seal is provided.

Figure 1B:
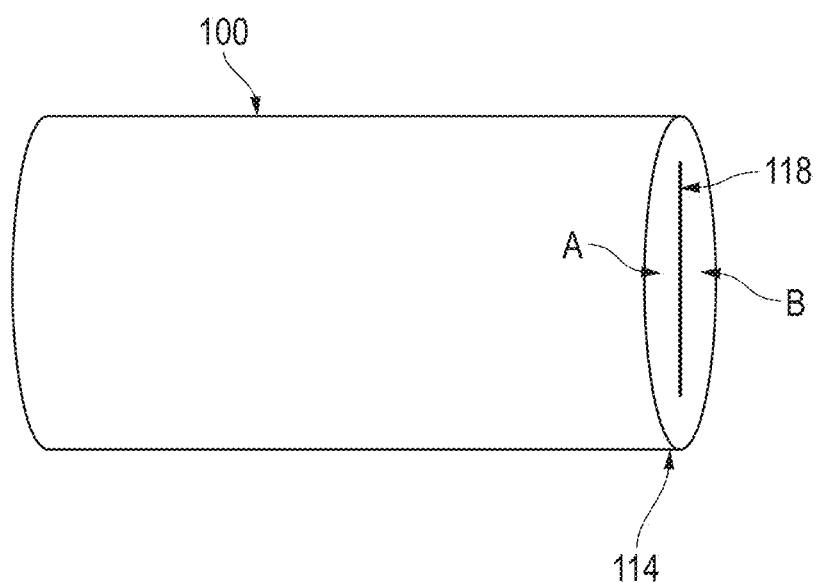
Figure 2:
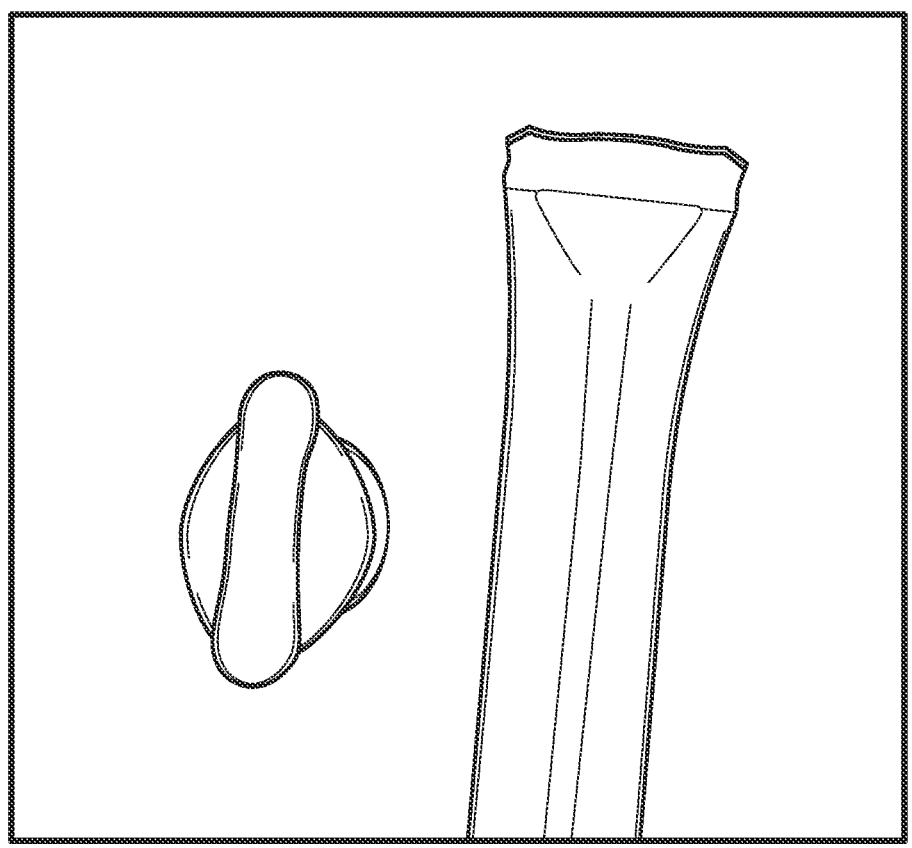
FIG. 2 includes an exemplary sealed profile.

For instance and as seen in FIG. 1B, the end 114 may be compressed such that the surface treated inner surface 112 forms a flat seal where a cross-section A of the inner surface 112 is sealed to an opposing side of the lumen, a cross-section B of the inner surface 112. In a particular embodiment, the inner surface 112 has a cross-section A that is in full and direct contact with a cross-section B across an opposing side of the lumen. Typically, a compression force of less than 100 Newtons (N) is applied to the end 114. Further, the compression may be applied for at least 1 second, at least 5 seconds, at least 10 second, at least 30 seconds, or even greater. An effective seal is provided by controlling the amount of surface area treated, such as a width of the surface area, as well as a width of the end of the tube that is compressed. In an embodiment, the width of the seal is at least 0.5 mm, such as at least 0.75 mm, such as at least about 1.0 mm, such as at least about 1.5 mm, such as at least about 2.0 mm, or even greater. In an embodiment, the sealed end has a mechanical strength greater than or equal to a mechanical strength of the sidewall. For instance, a structural integrity of the sidewall 110 will fail before a structural integrity of the sealed end structurally fails. As seen in FIG. 1B, the sealed end 118 closes the hollow bore 108 such that fluid can no longer flow therethrough. An exemplary sealed tube can also be seen in FIG. 2. Although the sealed end 118 is illustrated as the terminal end of a profile 100, a seal may be formed along any length of a profile where it is desired to terminate a fluid flow at a point.

The method may further including cutting the profile along a length of the profile, such as across an axis of the tube at any point along the length of the profile. For instance, the profile 100 has a lumen for fluid flow therethrough. In an exemplary embodiment, the profile has a proximal end, a distal end, and a length. At least the proximal end, the distal end, or combination thereof may be coupled to a fluid source. Any fluid source is envisioned. In a particular embodiment, a fluid source, such as a container, reactor, reservoir, tank, or bag, is coupled to the profile. The profile may engage and be coupled to a pump, fitting, valve, dispenser, or another container, reactor, reservoir, tank, bag, or combination thereof. In an example, the profile may be coupled to a water container and may have a dispenser fitting. In an example, it may be desirable to disconnect the fluid flow provided by the profile. To provide a sterile disconnection along the length of the profile, the profile may be cut and a sterile terminus may be provided. For instance, a sterile disconnection is provided by cutting the profile between the water container and the dispenser fitting. Any sterile terminus and disconnection may be provided along the length of the profile to provide the sealed end.

Any length of profile 100 may be envisioned. Any point of cutting the profile 100 is envisioned and is dependent upon the final length desired for the profile and the sealed end. For instance, a length of the profile may be cut to create at least one end. For instance, when the profile is cut along the length, two ends may be formed at a cutting point. Any method of cutting is envisioned and includes cutting with a blade, a laser, a plasma, or combination thereof. The blade may be at any temperature, such as a heated blade or a room temperature blade. In an embodiment and when the method includes plasma cutting, the plasma cutting and surface treatment may use the same activation energy to plasma cut and surface treat. In an embodiment, fluid flow may be stopped by the application of a clamp to the lumen. For instance, the clamp is applied prior to cutting the profile. In an embodiment, to provide a sterile disconnection, a surface adjacent to at least one cut end of the profile is surface treated and compressed to profile the sealed end. When a clamp is present to stop fluid flow, the clamp may then be removed after the end is sealed. Although described as cutting the profile and then providing a seal, any order of cutting and providing a seal is envisioned. In an embodiment, the profile is sealed and then subsequently cut along any length desired.

In a particular embodiment, the inner surface 112 of the profile 100 has a desirable surface roughness to provide a desirable seal. For instance, the inner surface 112 of the profile 100 has a Ra of less than about 20 μm, such as less than about 5 μm, such as less than about 1 μm, or even less than about 0.5 μm, as measured by a MarSurf M 300C Mobile Roughness Measuring Instrument. In an example, the surface activation treatment minimally changes a surface roughness of a treated surface. In an embodiment, the surface roughness of a treated surface of the profile changes by less than about 5%, such as less than about 2%, or even less than about 1%, compared to an untreated surface of the profile.

The sealed end has further advantageous physical and chemical properties. In an embodiment, the sealed end has a mechanical strength of at least 2%, at least 10%, or even at least 35% of a bulk material of the profile, testing conditions as described by the tensile test in the Examples. A measurement of "a bulk material" herein refers to an average measurement obtained over any sampling of the material that is not any portion of the surface that is treated. For instance, the sealed end has a failure mode of cohesive failure. Although not being bound by theory, a surface activation treatment at least excites an atom at a molecular level to provide the sealed end. For instance, the treated surface has an oxygen atomic concentration of greater than about 2%, such as greater than about 5%, such as greater than about 10%, or even greater than about 15%, compared to a bulk material of the profile via XPS. For instance, the treated surface has a nitrogen atomic concentration of greater than about 2%, such as greater than about 5%, such as greater than about 10%, or even greater than about 15%, compared to a bulk material of the profile via XPS. In a particular embodiment, the interface has a higher valence of an element, compared to a bulk material of the profile. Further, a surface tension at the interface is greater than about 20, such as greater than about 22, or even greater than about 25, as described by the surface energy test in the Examples. For instance, the treated surface has a surface tension of greater than about 20, such as greater than about 22, or even greater than about 25. In particular, a surface tension is increased at a treated surface of at least about 1 mM/m, at least about 3 mM/m, or even at least than about 10 mM/m, as described by the surface energy test in the Examples.

In a particular embodiment, the sealed end 118 prevents fluid flow through the hollow bore 108. Typically, the sealed end is substantially free of an external bonding material. Any external bonding material includes any mechanical fluid constraint, such as a mechanical clamp, screw, tie, or combination thereof, any external adhesive material, or combination thereof envisioned such as any added material that provides adhesive properties. Furthermore, the sealed end is substantially free of any reversible chemistry. "Reversible chemistry" as used herein refers to a chemical reaction that forms a new chemical compound that is different than an original chemical compound. In an embodiment, the surface activation does not increase a temperature of a treated surface to exceed the melting point of the bulk material.

In a particular embodiment, a sealed end is a sterile terminus provided for the profile 100. In an embodiment, at least the profile 100 is sterile prior to the sealed end. In an embodiment, the surface activation treatment provides a sterile terminus at a sealed end of the profile 100 or at least maintains sterility of a pre-sterilized profile 100. In an embodiment, the surface activation treatment sterilizes the treated surface of the profile 100. Although not illustrated, the surface activation treatment may be used to provide a visible bubble at the interface. The visible bubble may be advantageous as a visual indicator that a seal has been achieved or when the seal is no longer present.

As described, the surface activation treatment includes, in an embodiment, corona treatment, plasma treatment, ion treatment, or combination thereof. For instance, the corona treatment ionizes the atmosphere to activate a surface of the profile. In an embodiment, the surface activation treatment includes plasma treatment such as, for example, an inert gas plasma, an oxygen-containing plasma, a nitrogen-containing plasma, a fluorine-containing plasma, or combination thereof. In an embodiment, the surface activation treatment includes plasma treatment which ionizes a gas such as helium, neon, oxygen, argon, nitrogen, compressed air, ammonia, or combination thereof. In an embodiment, the surface activation treatment includes plasma treatment which ionizes a gas such as oxygen, argon, nitrogen, compressed air, ammonia, or combination thereof. Any conditions of the surface activation treatment are envisioned that provides a sealed end as well as sterile conditions for the profile. For instance, the plasma treatment is provided for less than 2 minutes, such as less than 1 minute, such as less than 45 seconds, such as less than 30 seconds, or even less than 10 seconds. In a particular embodiment, an extraction profile of the profile before and after surface activation treatment is substantially identical, indicating that the chemical composition of the profile has not changed before and after surface activation treatment. Furthermore, a change in particulates in the profile, such as the treated surface of the sealed end, before and after surface activation treatment is +/−5%, such as +/−15%, or even +/−50%. In an embodiment, the profile may be surface treated multiple times. For instance, the method can include cutting the sealed end, providing an additional surface activation treatment, and re-sealing the cut end.

Since the surface treatment provides sterility to the profile 100, a further sterilization process is not required. Further, the surface activation treatment provides an effective seal where the sealed end is substantially free of an adhesive, a primer, a chemical treatment, or combination thereof. Any energy, dependent on power and time, is envisioned that activates the surface of the profile. For examples, a power output is about 480 Watts for about 5 seconds.

In an embodiment, a reinforcement (not illustrated) can be used to reinforce the sealed end 118. In an embodiment, the reinforcement is a fastening device that surrounds at least a portion of the sealed end 118. In a particular embodiment, the fastening device surrounds the entire sealed end 118. Any fastening device is envisioned such as, for example, a clamp, a polymer tape, an overmolded polymer, a glue, or combination thereof. In a particular embodiment, the fastening device is a polymer tape such as a silicone tape. The silicone tape may be self-adhesive. In another embodiment, a surface between the polymer tape is surface treated to enhance the adhesion of the polymer tape to an exterior surface adjacent to the sealed end 118. For instance, the surface of the polymer tape is treated. In another embodiment, the outer surface of the sealed end 118 is treated. In a particular embodiment the surface between the polymer tape is surface treated with the surface activation treatment described for the sealing and sterilizing of the profile. Any sequence of surface treating the polymer tape concurrently or subsequently with surface treatment with the surface activation treatment for sealing is envisioned.

In exemplary embodiments, the profile with the sealed end can be used in a variety of applications where a sealed end is desired. In a particular embodiment, a sterile sealed end is achieved. Advantageously and in a particular embodiment, the surface activation treatment provides a method of sealing and sterilizing a multitude of polymeric materials not yet before sealed while maintaining a sterilized condition. In particular, the sterile nature of the seal is useful for any application where sterility is desired. For instance, the seal of any profile has potential for FDA, ADCF, USP Class VI, NSF, European Pharmacopoeia compliant, United States Pharmacopoeia (USP) compliant, USP physiochemical compliant, ISO 10993 Standard for evaluating biocompatibility of a medical device, and other regulatory approvals. In a particular embodiment, the profile is non-cytotoxic, non-hemolytic, non-pyrogenic, animal-derived component-free, non-mutagenic, non-bacteriostatic, non-fungistatic, or any combination thereof.

In an embodiment, the profile may be used in applications such as industrial, medical applications, health care, biopharmaceutical, drinking water, food & beverage applications, dairy applications, laboratory applications, FDA applications, and the like. In an exemplary embodiment, the method of providing a sterile terminus may be used in applications such as a fluid transfer tube in food and beverage processing equipment, a fluid transfer tube in medical and health care, biopharmaceutical manufacturing equipment, and peristaltic pump tube for medical, laboratory, and biopharmaceutical applications.

Many different aspects and embodiments are possible. Some of those aspects and embodiments are described herein. After reading this specification, skilled artisans will appreciate that those aspects and embodiments are only illustrative and do not limit the scope of the present invention. Embodiments may be in accordance with any one or more of the items as listed below.

Embodiment 1. A profile includes: a sidewall, a lumen for a fluid path, and an end, the profile including a thermoset material, wherein the profile includes a sealed end without an external bonding material, wherein the sealed end withstands a seal integrity pressure test of at least 1 psi, such as at least 5 psi, such as at least 10 psi, such as at least 15 psi, or even at least 20 psi air pressure for about 30 minutes under dry and wet conditions.

Embodiment 2. A profile includes: a sidewall, a lumen for a fluid path, and an end, the profile including a thermoset material, wherein the profile includes a sealed end without an external bonding material, wherein the sealed end has a mechanical strength greater than or equal to a mechanical strength of the sidewall.

Embodiment 3. The profile of any of the preceding embodiments, wherein the external bonding material includes a mechanical clamp, an adhesive, or combination thereof.

Embodiment 4. The profile of any of the preceding embodiments, wherein the sealed end is provided via surface activation treatment and compression of the lumen.

Embodiment 5. A method of providing a sterile terminus of a profile including: providing the profile having a sidewall, a lumen for a fluid path, and an end, the profile including a thermoset material; providing a surface activation treatment to a surface adjacent to the end of the profile; and sealing the end to provide the terminus of the lumen, wherein the sealed end has a mechanical strength greater than or equal to a mechanical strength of the sidewall.

Embodiment 6. A method of providing a sterile disconnection of a profile including: providing the profile having a sidewall and a lumen for a fluid path therethrough, the profile including a thermoset material; cutting the profile to create an end; providing a surface activation treatment to a surface adjacent to the end of the profile; and sealing the end to provide a terminus of the lumen, wherein the sealed end has a mechanical strength greater than or equal to a mechanical strength of the sidewall.

Embodiment 7. The method of providing the sterile terminus of the profile or the method of providing the sterile disconnection of the profile of any of embodiments 5-6, wherein sealing the end includes compressing the end of the profile to form a flat seal.

Embodiment 8. The method of providing the sterile disconnection of the profile of any of embodiments 6-7, wherein cutting the profile includes blade cutting, laser cutting, plasma cutting, or combination thereof.

Embodiment 9. The method of providing the sterile connection of the profile of any of embodiments 6-8, further including applying a clamp to the lumen to stop any fluid flow prior to cutting the profile.

Embodiment 10. The method of providing the sterile connection of the profile of embodiment 9, further including removing the clamp after the end is sealed.

Embodiment 11. The profile, the method of providing the sterile terminus of the profile, or the method of providing the sterile disconnection of the profile of any of embodiments 4-10, wherein an inner surface of the end is treated with the surface activation treatment.

Embodiment 12. The profile, the method of providing the sterile terminus of the profile, or the method of providing the sterile disconnection of the profile of any of the preceding embodiments, wherein the fluid includes liquid, gas, powder, solid, or combination thereof.

Embodiment 13. The profile, the method of providing the sterile terminus of the profile, or the method of providing the sterile disconnection of the profile of any of the preceding embodiments, wherein the thermoset material of the profile includes a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a halogenated rubber, a blend, or combination thereof.

Embodiment 14. The profile, the method of providing the sterile terminus of the profile, or the method of providing the sterile disconnection of the profile of any of the preceding embodiments, wherein the profile includes a silicone elastomer.

Embodiment 15. The profile, the method of providing the sterile terminus of the profile, or the method of providing the sterile disconnection of the profile of any of the preceding embodiments, wherein the profile includes a tubing, a port, a connector, a hose, a catheter, or combination thereof.

Embodiment 16. The profile, the method of providing the sterile terminus of the profile, or the method of providing the sterile disconnection of the profile of any of the preceding embodiments, wherein the sealed end has a mechanical strength of at least 2%, at least 10%, or even at least 35% of a bulk material of the profile.

Embodiment 17. The profile, the method of providing the sterile terminus of the profile, or the method of providing the sterile disconnection of the profile of any of embodiments 2-16, wherein the sealed end withstands a seal integrity pressure test of at least 1 psi, such as at least 5 psi, such as at least 10 psi, such as at least 15 psi, or even at least 20 psi air pressure for about 30 minutes under dry and wet conditions.

Embodiment 18. The profile, the method of providing the sterile terminus of the profile, or the method of providing the sterile disconnection of the profile of any of the preceding embodiments, wherein the sealed end maintains a burst of at least about 10%, such as at least about 15%, such as at least about 25%, or even at least about 50%, compared to a burst of the sidewall.

Embodiment 19. The profile, the method of providing the sterile terminus of the profile, or the method of providing the sterile disconnection of the profile of embodiment 18, wherein the sidewall bursts before burst at the seal.

Embodiment 20. The profile, the method of providing the sterile terminus of the profile, or the method of providing the sterile disconnection of the profile of any of the preceding embodiments, wherein the sealed end has an adhesion force of at least about 5 ppi, such as at least about 15 ppi, or even as at least about 50 ppi.

Embodiment 21. The profile, the method of providing the sterile terminus of the profile, or the method of providing the sterile disconnection of the profile of any of embodiments 4-20, wherein the surface activation treatment includes processing input energy to a surface of the profile with wave irradiation, particle irradiation, or combination thereof.

Embodiment 22. The profile, the method of providing the sterile terminus of the profile, or the method of providing the sterile disconnection of the profile of embodiment 21, wherein the wave irradiation includes microwaves, ultraviolet, x-rays, gamma radiation, or combination thereof.

Embodiment 23. The profile, the method of providing the sterile terminus of the profile, or the method of providing the sterile disconnection of the profile of embodiment 21, wherein the particle irradiation includes alpha radiation, beta radiation, charged ions, neutron radiation, or combination thereof.

Embodiment 24. The profile, the method of providing the sterile terminus of the profile, or the method of providing the sterile disconnection of the profile of embodiment 21, wherein the particle irradiation includes corona treatment, ion treatment, plasma treatment, or combination thereof.

Embodiment 25. The profile, the method of providing the sterile terminus of the profile, or the method of providing the sterile disconnection of the profile of any of the preceding embodiments, wherein the profile is used for biopharm applications, FDA applications, medical applications, laboratory applications, or combination thereof.

Embodiment 26. The profile, the method of providing the sterile terminus of the profile, or the method of providing the sterile disconnection of the profile of any of the preceding embodiments, wherein the sealed end has a failure mode of adhesive failure.

Embodiment 27. The profile, the method of providing the sterile terminus of the profile, or the method of providing the sterile disconnection of the profile of any of the preceding embodiments, wherein the sealed end has a failure mode of cohesive failure.

Embodiment 28. The profile, the method of providing the sterile terminus of the profile, or the method of providing the sterile disconnection of the profile of any of the preceding embodiments, wherein the treated surface of the sealed end has an oxygen atomic concentration of greater than about 2%, such as greater than about 5%, such as greater than about 10%, or even greater than about 15%, compared to a bulk material of the profile via XPS.

Embodiment 29. The profile, the method of providing the sterile terminus of the profile, or the method of providing the sterile disconnection of the profile of any of the preceding embodiments, wherein the sealed end has a higher valence of an element, compared to a bulk material of the profile.

Embodiment 30. The profile, the method of providing the sterile terminus of the profile, or the method of providing the sterile disconnection of the profile of any of the preceding embodiments, having a surface tension at the sealed end of greater than about 20, such as greater than about 22, or even greater than about 25.

Embodiment 31. The profile, the method of providing the sterile terminus of the profile, or the method of providing the sterile disconnection of the profile of any of the preceding embodiments, having a surface tension at a treated surface of greater than about 20, such as greater than about 22, or even greater than about 25.

Embodiment 32. The profile, the method of providing the sterile terminus of the profile, or the method of providing the sterile disconnection of the profile of any of the preceding embodiments, having a surface tension increase at a treated surface of at least about 1 mM/m, at least about 3 mM/m, or even at least than about 10 mM/m.

Embodiment 33. The profile, the method of providing the sterile terminus of the profile, or the method of providing the sterile disconnection of the profile of embodiment 32, wherein the profile includes a silicone elastomer.

Embodiment 34. The method of providing the sterile terminus of the profile or the method of providing the sterile disconnection of the profile of any of the preceding embodiments, wherein the sealed end is substantially free of any external bonding material.

Embodiment 35. The method of providing the sterile terminus of the profile or the method of providing the sterile disconnection of the profile of any of the preceding embodiments, wherein the external bonding material includes a mechanical clamp, a screw, a tie, an adhesive, or combination thereof.

Embodiment 36. The profile, the method of providing the sterile terminus of the profile, or the method of providing the sterile disconnection of the profile of any of the preceding embodiments, wherein the sealed end is substantially free of any reversible chemistry.

Embodiment 37. The profile, the method of providing the sterile terminus of the profile, or the method of providing the sterile disconnection of the profile of any of embodiments 4-36, wherein the surface activation does not increase a temperature of a treated surface to exceed the melting point of the bulk material.

Embodiment 38. The profile of embodiment 4, wherein the surface activation treatment provides a sterile seal.

Embodiment 39. The profile, the method of providing the sterile terminus of the profile, or the method of providing the sterile disconnection of the profile of any of the preceding embodiments, further comprising a visible bubble at the sealed end.

Embodiment 40. The profile, the method of providing the sterile terminus of the profile, or the method of providing the sterile disconnection of the profile of any of the preceding embodiments, wherein the profile is coupled to a pump, a fitting, a valve, a dispenser, a container, a reactor, a reservoir, a tank, a bag, or combination thereof.

Embodiment 41. The method of providing the sterile terminus of the profile or the method of providing the sterile disconnection of the profile of any of the preceding embodiments, wherein an extraction profile of the sealed end before and after surface activation treatment is identical.

Embodiment 42. The method of providing the sterile terminus of the profile or the method of providing the sterile disconnection of the profile of any of the preceding embodiments, wherein a change in particulates in the treated surface of the sealed end before and after surface activation treatment is +/−5%, such as +/−15%, or even +/−50%.

The concepts described herein will be further described in the following examples, which do not limit the scope of the disclosure described in the claims. The following examples are provided to better disclose and teach processes and compositions of the present invention. They are for illustrative purposes only, and it must be acknowledged that minor variations and changes can be made without materially affecting the spirit and scope of the invention as recited in the claims that follow.

Examples

General Procedure for Sealing an End and Burst Test:

Sealing: placed a tube under plasma, exposed at least an inner surface adjacent the end to plasma for a certain time; then immediately after the treatment, compressed the tubes and "seal" them by applying gentle compression force (less than 100 N but making sure the ends are in full contact).

Post treatment of tubing: the welded tubing was stored in ambient temperature and pressure for certain period before connecting to compression air for burst pressure test.

Burst Test Pressure Procedure

The pressure was provided via connecting to a compression air line with a regulator to control the pressure during the test. The open end of the "sealed" tubing was connected to the regulator using braid reinforcing silicone tubing with proper fitting. The whole tubing was immersed in water during the test. The failure of the tubing (burst at the seal or burst of tubing) could be easily indicated by the air bubble in the water tank. When the test began, the pressure was increased by controlling the regulator with the rate about 2 psi/s. The highest pressure through the regulator without any observed air bubbles in the tank, indicating burst, during the test was recorded. The whole process was also recorded by video and confirmed all the readings were correct after test.

Standard Operating Procedure of the Test:
1. Connected the welded tubing to the test apparatus.
2. Laid the pressure testing apparatus on a flat surface.
3. Filled the water tank with enough water to submerge test specimens.
4. Connected pressure testing apparatus to a clean, dry compressed air supply.
5. Determined the correct multi-barb fitting sizes for the tubing to be tested. Slightly oversized barbed fittings were acceptable as long as they do not cause the tubing to leak at the barbed fitting.
6. Installed the open end of the specimen on to the barbed fitting and secured with at least 1 zip tie.
7. Slowly pressurized the apparatus (~2 psi/s) until air bubbles were observed in the water tank.
8. Cleaned and dried the apparatus to repeat the test as necessary, in general, at least 3 samples were tested for one condition.

The tubing inner surface from extrusion was very smooth, therefore, the bonding at the interface was so good that the seal would be preserved, even the tubing burst in the test. Notably, the 50 duro tubing burst before breaking the seal, with ~¼ inch seal width. However, the seal could be broken when tubing had a higher burst pressure. For the 65 duro tubing, the seal was burst at about 46 psi, compared to the burst pressure of 51 psi. In either case, the sealing performance was desirable, particularly for biopharmaceutical applications.

Surface treatment conditions included plasma for 5 seconds. The tubing was then compressed and flattened by mechanical clamp for at least 30 seconds. The clamp was removed. The burst pressure was tested at least 2 hours after the sealing.

Results can be seen in Table 1 below. The control was the burst pressure of the tubing, tested using the burst pressure test procedure described above.

TABLE 1

| | Burst pressure (psi) | |
|---|---|---|
| Material | Control | Plasma sealed |
| 50 durometer silicone tubing with ½ inch ID and ¾ inch OD | 42 | 42 |
| 65 durometer silicone tubing with ½ inch ID and ¾ inch OD | 51 | 46 |

Surface Tension was Tested Via the Following Conditions:

Plasma welding surface energy of C-Flex and silicone tubing after exposure to plasma for welding procedure conditions and results were as follows.

Description of the tested materials is seen in Table 2.

TABLE 2

| Reference | Description |
|---|---|
| Silicone control | Control silicone samples (no plasma) |
| Silicone plasma treated surface | Silicone, adjacent to plasma treated surface |

ASTM D7334-08, "Standard Practice for Surface Wettability of Coatings, Substrates and Pigments by Advancing Contact Angle Measurement" was followed. This practice deals with the measuring of contact angles to characterize the wettability of surfaces. Two different solvents were used: water and diiodomethane (MI).

The instrument used was a Kruss Mobile Surface Analyzer, which uses an automatic liquid dispenser to place drops of solvent (volume=~1 µL) on a sample. Drops of water and MI were placed in parallel and allowed to settle on the surface. The values of the two contact angles were determined using drop shape analysis. 5+ drops of each solvent were tested on each sample surface.

For analysis, the Owens-Wendt method was used, which utilizes both the dispersive and polar components of each solvent to determine the surface energy components of the samples. The equation for the method follows:

$$\frac{\sigma_L(\cos\theta + 1)}{1\sqrt{\sigma_L^D}} = \frac{\sqrt{\sigma_S^P}\sqrt{\sigma_L^P}}{\sqrt{\sigma_L^D}} + \sqrt{\sigma_S^D}$$

Where: cos θ: Cosine of the contact angle of the liquid drop on the sample;

$\sigma_L$: Surface tension of the liquid;

$\sigma_L^D$: Dispersive component of the surface tension of the liquid;

$\sigma_L^P$: Polar component of the surface tension of the liquid;

$\sigma_S^D$: Dispersive component of the surface energy of the sample;

$\sigma_S^P$: Polar component of the surface energy of the sample.

The equation fits a linear equation y=mx+b. By fitting a linear regression using the mean contact angle of each drop and liquid surface tension components, the surface energy components of the sample was determined.

Contact angle measurements and surface energy calculations are shown in Table 3 and 4 below:

TABLE 3

Contact angle measurements

| Sample ID | Mean Water CA (°) | TD | Mean MI CA (*) | STD |
|---|---|---|---|---|
| Silicone control | 101.6 | .7 | 98.5 | 3.6 |
| Silicone plasma treated surface | 93.9 | 5 | 73.0 | 3.8 |

TABLE 4

Surface energy calculations

| | Surface Energy | | | | | |
|---|---|---|---|---|---|---|
| Sample ID | Surface Free Energy [mN/m] | TD | Dispersive [mN/m] | TD | Polar [mN/m] | TD |
| Silicone control | 13.6 | .5 | 9.2 | .3 | 4.4 | .2 |
| Silicone plasma treated surface | 24.3 | .2 | 21.2 | .1 | 3.0 | .1 |

Peel Test Conditions were as Follows:

The adhesion strength was measured by the following procedure. Preparation of the sample: Two silicone slabs with ~1/16 inch thick were stacked and welded by plasma. The welded silicone slabs was cut into ¼ inch wide pieces. The welded slabs were then placed in the instron with each slab gripped, and peeled with T shape/180 degree peel. The peel force was 9.9±3.9 ppi.

Extraction Profile was Determined as Follows:

The control silicone tubing and welded silicone tubing were extracted using 50% water and 50% of ethanol for 24 hours at 70° C. Then Gas Chromatograph/Mass Spectrometry was used to analyze the extraction profile. Notably, plasma welding did not substantially change the extraction profile of a material, such as silicone tubing. In an example, when comparing a silicone control and a plasma welded silicone, plasma welding did not increase the extraction of siloxanes.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A profile comprises: a sidewall, a lumen for a fluid path, and an end, the profile comprises a thermoset silicone elastomer material, wherein the profile comprises a sealed end without an external bonding material, wherein the sealed end withstands a seal integrity pressure test of at least 1 psi air pressure for about 30 minutes under dry and wet conditions.

2. The profile in accordance with claim 1, wherein the external bonding material comprises a mechanical clamp, an adhesive, or combination thereof.

3. The profile in accordance with claim 1, wherein an inner surface of the end is treated with a surface activation treatment.

4. The profile in accordance with claim 1, wherein the sealed end is provided via surface activation treatment and compression of the lumen.

5. The profile in accordance with claim 1, wherein the thermoset silicone elastomer material of the profile consists essentially of the silicone elastomer.

6. The profile in accordance with claim 1, wherein the sealed end has a failure mode of cohesive failure.

7. A profile comprises:
a sidewall, a lumen for a fluid path, and an end, the profile comprising a thermoset silicone elastomer material, wherein the profile comprises a sealed end without an external bonding material, wherein the sealed end has a mechanical strength greater than or equal to a mechanical strength of the sidewall.

8. The profile in accordance with claim 7, wherein the external bonding material comprises a mechanical clamp, an adhesive, or combination thereof.

9. The profile in accordance with claim 7, wherein the sealed end is provided via surface activation treatment and compression of the lumen.

10. The profile in accordance with claim 7, wherein an inner surface of the end is treated with a surface activation treatment.

11. The profile in accordance with claim 7, wherein the thermoset material of the profile consists essentially of the silicone elastomer.

12. The profile in accordance with claim 7, wherein the sealed end has a failure mode of cohesive failure.

* * * * *